United States Patent [19]

Eberle

[11] Patent Number: 4,688,513
[45] Date of Patent: Aug. 25, 1987

[54] CENTRIFUGAL CHAMBER WITH REMOVABLE CARRIER PLATE

[76] Inventor: Gunter Eberle, Gartenstrasse 100, 7200 Tuttlingen, Fed. Rep. of Germany

[21] Appl. No.: 607,278

[22] Filed: May 4, 1984

[30] Foreign Application Priority Data

May 4, 1983 [DE] Fed. Rep. of Germany ....... 3316336

[51] Int. Cl.$^4$ ............................................. B05C 3/18
[52] U.S. Cl. ..................................... 118/52; 118/415; 118/503; 494/16
[58] Field of Search ................... 494/16; 118/52, 415, 118/503

[56] References Cited

U.S. PATENT DOCUMENTS 3,457,897 7/1969 Warren ........................... 118/415 X
3,937,581 2/1976 Rodel et al. .......................... 494/10

Primary Examiner—John P. McIntosh
Attorney, Agent, or Firm—Antonelli, Terry & Wands

[57] ABSTRACT

A centrifugal chamber for coating slides with a sedimentation product of a sample fluid includes an upper part with at least one cylindrical sample chambers located therein, and a slide resting in sealed fashion against one end of the sample chambers. The slide is mounted on a flat surface of a carrier plate and is releasably connected with the assembly. The releasable connection between the upper part of the centrifugal chamber and the carrier plate which holds the slide includes a locking slide operable with one hand, with locking openings, and with the slide being displaceably mounted in the carrier plate in a longitudinal direction thereof and being further connectable with matching parts of the upper part which engage the locking openings.

5 Claims, 21 Drawing Figures

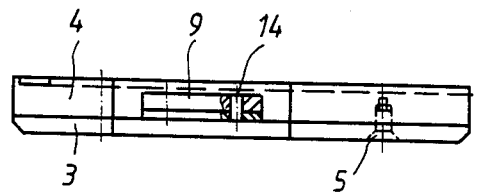
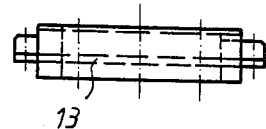
FIG 7    FIG 8
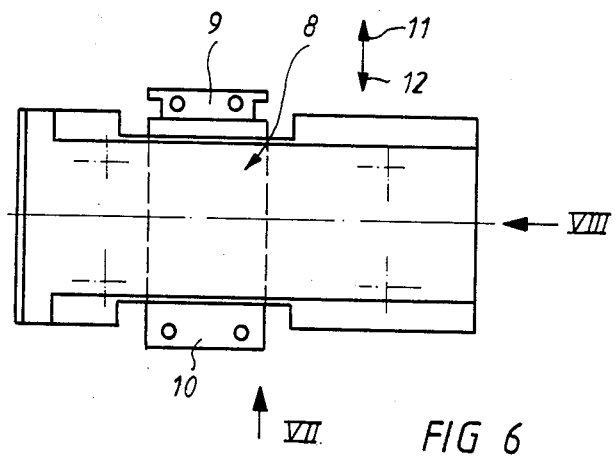
FIG 6
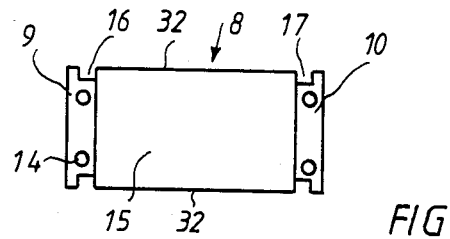
FIG 8A

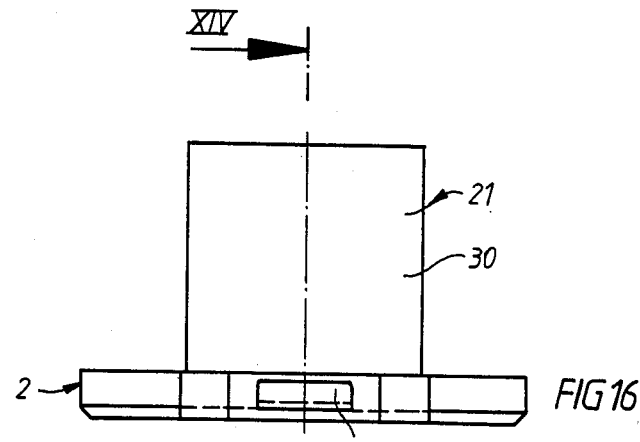
FIG 16
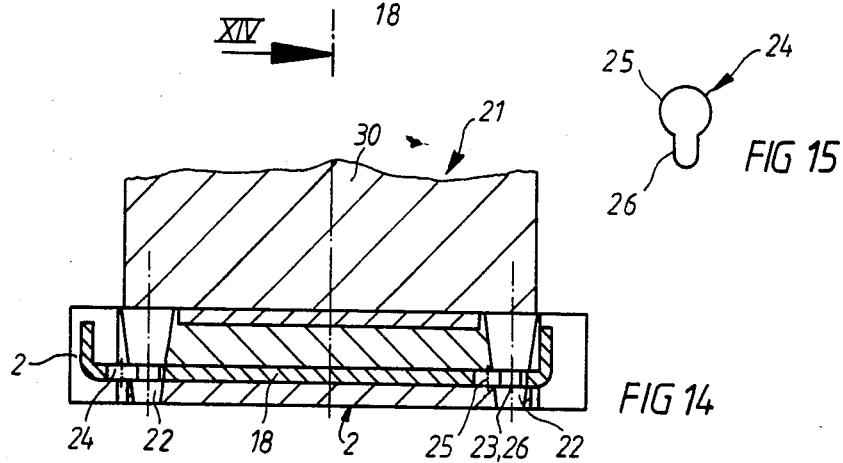
FIG 15
FIG 14
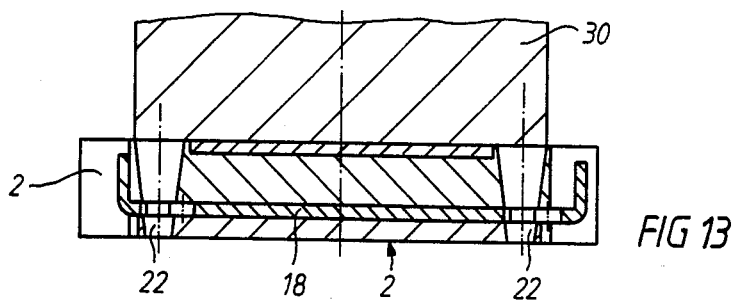
FIG 13

CENTRIFUGAL CHAMBER WITH REMOVABLE CARRIER PLATE

The invention relates to a centrifugal sample chamber for coating slides with a sedimentation product of a sample fluid during a centrifuging process, with the chamber including an upper part with at least one cylindrical sample chamber disposed therein, and a slide abutting one end of the sample chamber in a locking fashion, said slide being mounted on a flat surface of a carrier plate, said plate being releasably connected with the assembly.

German Patent Application P 32 32 581.9 proposes a centrifugal sample chamber of the aforementioned type; however, in the proposed sample chamber it is relatively difficult to remove the slide from the centrifugal chamber because a spring clip is provided at each end of the carrier plate, with the clip being releasably connectable with an upper part of the chamber. In order to remove the upper part from the carrier plate to, for example, remove the slide, one spring clip must be gripped with the hand and pulled outward, whereby it is possible only with difficulty to remove the upper part from the carrier plate in the same work step. The goal of the present invention, essentially resides in providing a sample chamber wherein the connection between the upper part of a centrifugal chamber and a carrier plate is more rapidly releasable.

To achieve the stated goal, the invention is characterized by the releasable connection between the upper part of the centrifugal chamber and the carrier plate holding the slide including a locking slide with locking openings, operable with one hand, with the slide being displacably mounted in the direction of a longitudinal axis axis of the carrier plate, and with the slide being connectable with associated parts of the upper part which engage the locking openings.

Therefore, a feature of the invention is that the locking slide provided according to the invention is operable with one hand. For this purpose, the centrifugal chamber is taken between the fingers of one hand, whereby, for example, the thumb of one hand rests against one side of the centrifugal chamber, while the remaining fingers rest on the opposite side of the locking slide. The locking slide is then slid in a longitudinal direction or, in another embodiment, rotated, whereby it is important that this be performed with the other fingers of this hand. After the locking slide has been released, the same hand can be used to pull the upper part away from the carrier plate, to, for example, change the slide.

In accordance with advantageous features of the present invention the upper part of the sample chamber is connected at least partially with bent hook ends of locking hooks gripping beneath the underside, with the hooks, in an open state, engaging the corresponding locking openings in the longitudinal edges of the locking slide and gripping beneath the locking slide in the closed state.

The locking hooks provided on the underside of the upper part are stable and, because of their multiple symmetrical arrangement, simultaneously allow the upper part, removed from the carrier plate, to be mounted on a support.

Advantageously, in accordance with the present invention, the upper part is connected with axial locking pins mounted on the bottom, each of the pins having an annular groove of reduced diameter and being adapted to be accommodated in a key hole-shaped locking opening in the locking slide. In the open position, the locking pin engages the larger-diameter opening in the locking opening and in the closed state the annular groove engages the smaller-diameter opening in the locking opening.

This embodiment is characterized by the simple design of the locking pins. The simple design of the locking slide is common to both the embodiments recited hereinabove.

In accordance with further features of the present invention, a rotatably mounted locking slide with an eccentric outer circumference is provided instead of a longitudinal displaceable locking slide, with the rotatably mounted locking slide being lockable by means of locking openings disposed on the outer circumference with matching parts of the upper part of the centrifugal chamber.

Instead of a longitudinally displaceable locking slide, therefore, rotation of a rotatably mounted locking slide can be provided. This embodiment comprises all of the advantages of the embodiments recited hereinabove, i.e. one-handed operation is possible at low structural and assembly cost.

In all the locking slides of the present invention, it is preferable that, in the open state (i.e. when the upper part rests on the carrier plate when the locking slide is in the open position), the slides extend far beyond the outside dimensions of the carrier plate, thereby preventing the entire centrifugal chamber from being placed in the corresponding chamber of a centrifuge with the locking slide in the open position, resulting in centrifuging in the open position, which would cause the sample contents to escape.

The subject of the present invention consists not only of the subject of the individual claims, but also the combination of the individual claims with each other.

All of the information and features disclosed in the documents, especially the three-dimensional design shown in the drawings, are claimed as essential to the invention to the extent that they are novel either individually or in combination with respect to the state of the art.

The invention is described in greater detail hereinbelow with reference to drawings showing several embodiments. Additional features and advantages of the invention essential thereto are apparent from the drawings and their description.

FIG. 6 is a top view of the carrier plate of a centrifugal chamber according to FIGS. 1-3;

FIG. 7 is a side view of the carrier plate with a partial section through the locking slide;

FIG. 8 is an end view of the carrier plate taken in the direction of arrow III in FIG. 6;

FIG. 8a is a top view of the locking slide;

FIG. 13 is a section through a centrifugal chamber in a second embodiment in the unlocked state;

FIG. 14 is a section taken along the line XIV—XIV in FIG. 16 through the centrifugal chamber in the locked state;

FIG. 15 is a top view of the locking opening in the locking slide;

FIG. 16 is an end view of the centrifugal chamber shown in FIGS. 13 and 14;

Figures 2, 3:
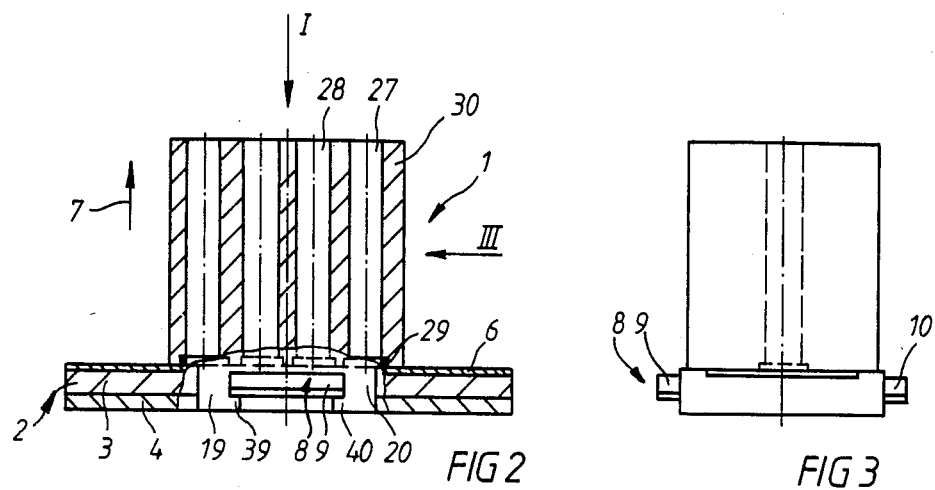
FIG. 2 is a central longitudinal section through the centrifugal chamber shown in FIG. 1.
FIG. 3 is an end view of the centrifugal chamber taken in the direction of arrow III in FIG. 2.
Figure 1:
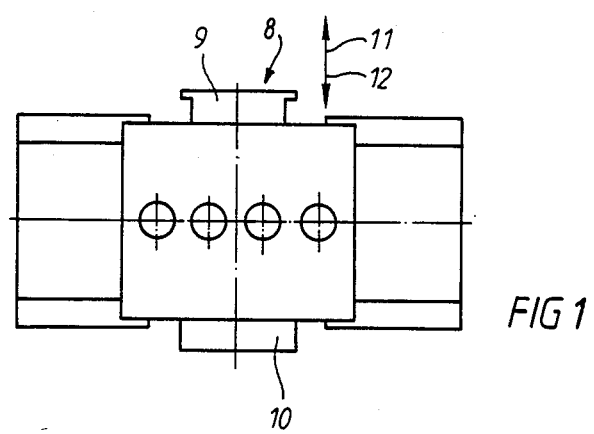
FIG. 1 is a top view in the direction of arrow I of a centrifugal chamber in a first embodiment according to FIG. 2.

Referring now to the drawings wherein like reference numerals are used throughout the various views to designate like parts and, more particularly, to FIGS. 1–3, according to these figures, a centrifugal chamber generally designated by the reference numeral 1 includes an upper part 30 and a carrier plate generally designated by the reference numeral 2 releasably connected therewith, with the carrier plate 2 being formed of two partial plates 3, 4 connected together by screws 5 (FIG. 7). A slide 6, in the shape of a rectangular glass plate, is disposed on top of the carrier plate 2.

Upper part 30 is fashioned of a transparent plastic material having a plurality of axially extending and hollow cylindrical sample chambers 27, 28 therein with the chambers 27, 28 being formed by machined bores. In use, the sample chambers 27, 28 are filled with a sample liquid and the centrifugal chamber 1 is placed in a centrifuge and centrifuged therein. The sample liquid is separated, and the sedimentation product is deposited onto the corresponding fields of slide 6 under the influence of the centrifugal force which acts downward in the longitudinal direction of the sample chambers 27, 28.

A gasket 29 is interposed between an underside of upper part 30 and the slide 6 so that no liquid can escape from sample chambers 27, 28 during the centerfuging process.

After the centerfuging process is complete, the upper part 30 is removed from carrier plate 2 to remove slide 6 and subject the sample fields deposited on slide 6 to further investigation.

According to the invention a quick-acting lock is provided between upper part 30 and carrier plate 2, with the lock being operable only with the fingers of one hand. The quick acting lock includes a locking slide by generally designated the reference numeral 8 (FIG. 8a) displaceably mounted in an opening in the carrier plate 2 as shown in FIG. 1, to move in the direction of arrows 11 and 12 (FIGS. 1 and 6), i.e. longitudinally. In the unlocked state, upper part 30 can be lifted off the carrier plate 2 in the direction of the arrow 7 (FIG. 2), and the slide 6, located therebelow, can be removed from carrier plate 2.

Figure 5:
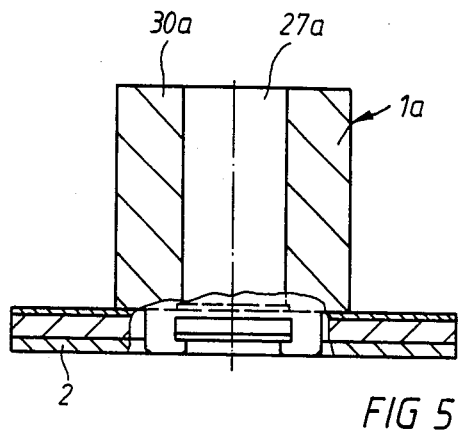
FIGS. 4 and 5 show a modified embodiment relative to the upper part with the same carrier plate and the same locking slide.
Figure 4:
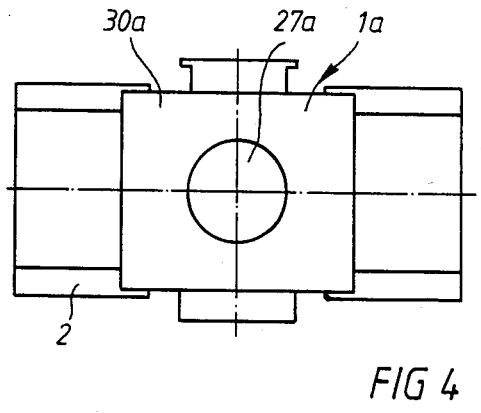

As shown in FIGS. 4 and 5 the carrier plate 2 can also be combined with upper part 30a of any other shape, resulting in a centrifugal chamber generally designated by the reference numeral 1a containing only a single sample chamber 27a in the upper part 30a. As shown in FIG. 8a, the locking slide 8 is provided with two side handles 9, 10.

Figures 9, 10:
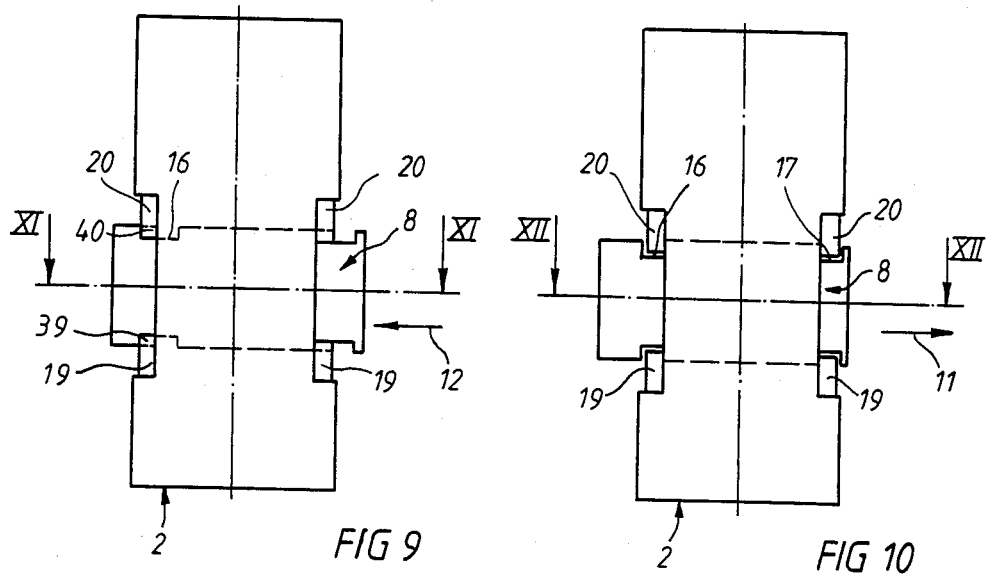
FIG. 9 is a top view of the bottom of the carrier plate looking in the direction of arrow IX in FIG. 11, in the locked state.
FIG. 10 is a top view of the bottom of the carrier plate in the unlocked state.

It is essential to the present invention that centrifugal chamber 1 or 1a can be taken between the fingers of one hand so that, for example, as shown in FIG. 9, the thumb of one hand rests on the left side of the carrier plate while the remaining fingers on the right side of the carrier plate longitudinally displace locking slide 8 in the direction of arrow 12, so that the locking slide 8 assumes an unlocked position shown in FIG. 10. Upper part 30 can then be removed in the direction of arrow 7 from carrier plate 2 using the same hand. Likewise, the connection between upper part 30 and carrier plate 2 is produced, as shown in FIG. 10, by moving locking slide 8 to the right in the direction of arrow 11, thereby firmly locking the upper part 30 to carrier plate 2.

Figures 11, 12:
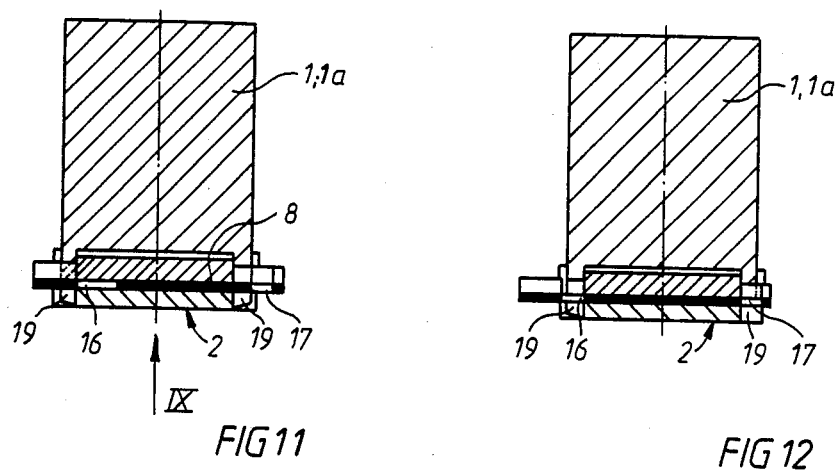
FIG. 11 is a section taken along the line XI—XI in FIG. 9.
FIG. 12 is a section taken along the line XII—XII in FIG. 10.
Figure 18:
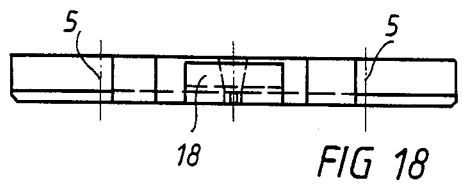
FIG. 18 is a side view of the carrier plate.
Figure 19:
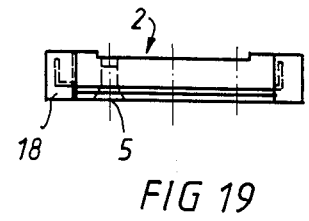
FIG. 19 is an end view of the carrier plate.
Figure 17:
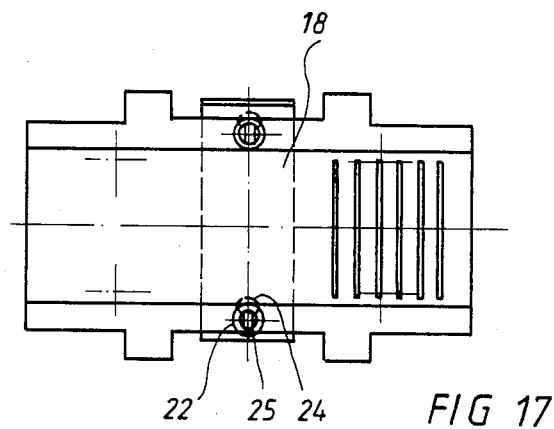
FIG. 17 is a bottom view of the carrier plate.

The releasable connection between carrier plate 2 and upper part 30, according to the first embodiment shown in FIGS. 1 to 12, is produced by locking hooks 19, 20 disposed on the underside of the upper part 30, with each of the hooks 19, 20 tapering to a lower bent hook end 39, 40. Locking hooks 19 and 20 grip beneath locking slide 8 with their hook ends 39, 40. In the unlocked state shown in FIGS. 10 and 12, hook ends 39, 40 rest in the matching locking openings 16, 17 of the locking slide 8 made somewhat larger (see FIG. 8a) corresponding to the unlocked position. When the locking slide 8 is moved to the right in the direction of arrow 11, as shown in FIGS. 10 and 12, the inwardly bent hook ends 39, 40 come in contact with locking pieces 32, 33 adjoining each of the locking openings 16, 17 (see FIG. 8a). Hook ends 39 and 40 therefore are located below locking pieces 32, 33 and grip beneath these locking pieces 32, 33 resulting in the locked state shown in FIGS. 9 and 11. FIG. 7 shows that handles 9 and 10 are made of molded plastic parts, connected to the middle part 15 of locking slide 8, made of metal, by pins 14.

As shown in FIG. 8 a groove 13 is provided in carrier plate 2 between the two partial plates 3 and 4 thereof. The design of carrier plate 2 is considerably simplified by dividing carrier plate 2 into two partial plates 3 and 4 mounted parallel to each other, forming groove 13 between them.

As shown in FIGS. 13–17, locking pins 22 are formed on an underside of upper part 30 of a centrifugal chamber generally designated by the reference numeral 21 with the pins 22 having a frustroconical shape. An annular groove 23 of reduced diameter is machined into the outer surface of the locking pin 22. As shown in FIG. 15, locking openings generally designated by the reference numeral 24, machined into both sides of the locking slide 18, include a larger-diameter opening 25 and a smaller opening 26 immediately adjacent to and merging with large opening 25. The diameter of opening 25 is chosen so that it is slightly larger than the maximum outside diameter of the locking pin 22 in the vicinity of the locking slide 18.

The diameter 26 of the opening is smaller than the maximum outside diameter of locking pin 22, but larger than the diameter of annular groove 23. FIG. 13 shows the unlocked position, from which it is evident that locking pin 22 is located in the vicinity of the larger opening 25, so that upper part 30 can be removed from carrier plate 2. locking pin 22 is located in a vicinity of the larger opening 25 of locking opening 24.

Figure 20:
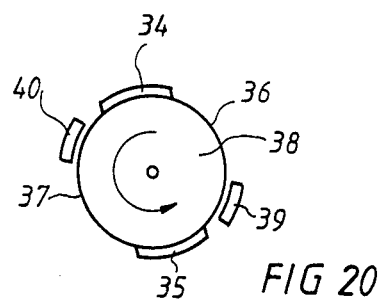
FIG. 20 is a schematic representation of an additional embodiment showing a rotatably mounted locking slide.

In FIG. 20, rather than a linearly displaceable locking slide 8, 18, for the lock between upper part 30 and carrier plate 2, a rotatable locking slide 38 is provided which is either mounted completely eccentrically in a first embodiment or, in the embodiment shown in FIG. 20, mounted centrally, and comprises locking pieces 34, 35 on its outer circumference, with the locking pieces 34, 35 having a greater radial distance from the pivot point than locking openings 36, 37 adjacent thereto. Upper part 30, according to the embodiments described initially above in FIGS. 1–13, is again provided with locking hooks 19, 20 abutted by inwardly bent hook ends 39, 40, with the hook ends 39, 40 being directed at the pivot point of locking slide 38. By rotating locking slide 38, either locking pieces 34, 35 enter the vicinity of hook ends 39, 40, so that the locked position is assumed, while further rotation causes hook ends 39, 40 to disengage from locking pieces 34, 35 and to move into the vicinity of lock openings 36, 37 so that the upper part 30 can be removed from carrier plate 2.

I claim:

1. Centrifugal chamber for coating a slide with a sedimentation product of sample fluid during a centrifuging process, the chamber including an upper part with at least one cylindrical sample chamber disposed therein, a slide abutting one end of the at least one sample chamber, a carrier plate having said slide mounted on a flat surface thereof, means for releasably connecting the carrier plate with the upper part, said means including a locking slide being provided with locking openings, means provided in said carrier plate for allowing movement of the locking slide with respect to the carrier plate, and means provided on said upper part for passing through the locking openings in and engaging the locking slide.

2. Centrifugal chamber according to claim 1, wherein the means for engaging the locking slide includes locking hooks having bent hook ends for at least partially engaging the locking slide, said hooks, in an open state, engaging the locking openings along longitudinal edges of the locking slide, and, in a closed position, gripping beneath the locking slide whereby said locking slide is displaceable in a longitudinal direction.

3. Centrifugal chamber according to claim 1 wherein the engaging means includes axially extending locking pins mounted on a bottom of the upper part, each of said pins having an annular groove of a reduced diameter, said locking openings having a substantially keyhole-shaped configuration whereby, in an open state, the respective locking pins engage a larger-diameter portion of the locking opening and, in a closed state, the annular groove engages a smaller-diameter portion of the locking opening.

4. Centrifugal chamber according to claim 1, wherein the locking slide, in an open state, projects beyond the outer dimensions of the carrier plate at least on one side thereof.

5. Centrifugal chamber according to claim 2, wherein the locking slide, in an open state, projects beyond the outer dimensions of the carrier plate at least on one side thereof.

* * * * *